US011167138B2

(12) United States Patent
Patel et al.

(10) Patent No.: US 11,167,138 B2
(45) Date of Patent: Nov. 9, 2021

(54) METHOD AND DEVICE FOR DEEP BRAIN STIMULATION

(71) Applicant: BIOINDUCTION LIMITED, Bristol (GB)

(72) Inventors: Nikunj Patel, Bristol (GB); Ivor Stephen Gillbe, Bristol (GB)

(73) Assignee: Bioinduction Limited

( * ) Notice: Subject to any disclaimer, the term of this patent is extended or adjusted under 35 U.S.C. 154(b) by 0 days.

(21) Appl. No.: 15/040,563

(22) Filed: Feb. 10, 2016

(65) Prior Publication Data

US 2016/0367809 A1 Dec. 22, 2016

(51) Int. Cl.
*A61N 1/36* (2006.01)
*A61N 1/05* (2006.01)
*A61N 5/06* (2006.01)

(52) U.S. Cl.
CPC ....... *A61N 1/36064* (2013.01); *A61N 1/0534* (2013.01); *A61N 5/0622* (2013.01); *A61N 1/36082* (2013.01); *A61N 1/36096* (2013.01); *A61N 1/36117* (2013.01); *A61N 1/36171* (2013.01); *A61N 5/06* (2013.01); *A61N 5/0601* (2013.01); *A61N 5/0618* (2013.01); *A61N 2005/0612* (2013.01)

(58) Field of Classification Search
CPC .............. A61N 1/0534; A61N 1/36082; A61N 1/36096
See application file for complete search history.

(56) References Cited

U.S. PATENT DOCUMENTS

| 6,909,917 | B2 | 6/2005 | Woods et al. |
| 8,515,541 | B1* | 8/2013 | Jaax ..................... A61N 1/0531 |
| | | | 607/116 |
| 8,612,018 | B2 | 12/2013 | Gillbe |
| 2005/0049651 | A1 | 3/2005 | Whitehurst |
| 2006/0004422 | A1* | 1/2006 | De Ridder ........... A61N 1/0529 |
| | | | 607/45 |
| 2006/0041283 | A1 | 2/2006 | Gelfand et al. |
| 2006/0212090 | A1* | 9/2006 | Lozano .............. A61N 1/36071 |
| | | | 607/45 |
| 2007/0191903 | A1* | 8/2007 | Bruinstroop ...... A61M 5/14276 |
| | | | 607/42 |
| 2007/0203537 | A1 | 8/2007 | Goetz |

(Continued)

FOREIGN PATENT DOCUMENTS

| CN | 204092843 U | 1/2015 |
| GB | 2357700 A | 7/2001 |

(Continued)

OTHER PUBLICATIONS

Jens Hubner, International Search Report and The Written Opinion of the International Searching Authority, dated Oct. 19, 2016, 14 pages, European Patent Office, Munich.

(Continued)

*Primary Examiner* — George R Evanisko
(74) *Attorney, Agent, or Firm* — McGarry Bair PC

(57) ABSTRACT

A method of treating Alzheimer's Disease and/or Multiple Sclerosis and/or Minimally Conscious State and/or Mood Disorders and/or vascular brain disorders where there is small vessel compromise in a subject in need thereof, comprising applying a neuromodulation signal to the 1PAG or v1PAG of the subject.

12 Claims, 6 Drawing Sheets

(56) References Cited

U.S. PATENT DOCUMENTS

| | | |
|---|---|---|
| 2008/0269854 A1 | 10/2008 | Hegland et al. |
| 2008/0288018 A1* | 11/2008 | Rezai .................. A61B 5/16 607/45 |
| 2009/0005833 A1 | 1/2009 | Cameron et al. |
| 2009/0157141 A1* | 6/2009 | Chiao .................. A61N 1/36071 607/46 |
| 2010/0268298 A1 | 10/2010 | Moffitt et al. |
| 2011/0160797 A1 | 6/2011 | Makous |
| 2013/0282075 A1 | 10/2013 | De Ridder |
| 2013/0289385 A1 | 10/2013 | Lozano et al. |
| 2013/0317572 A1 | 11/2013 | Zhu et al. |
| 2013/0317575 A1 | 11/2013 | Zhu et al. |
| 2014/0039450 A1* | 2/2014 | Green .................. A61N 1/3611 604/503 |
| 2014/0130349 A1 | 5/2014 | Swanson et al. |
| 2016/0089532 A1 | 3/2016 | Dou |

FOREIGN PATENT DOCUMENTS

| | | |
|---|---|---|
| WO | 200160450 A1 | 8/2001 |
| WO | 2004069328 A2 | 8/2004 |
| WO | 2006041870 A2 | 4/2006 |
| WO | 2006094072 A2 | 9/2006 |
| WO | 2007007058 A1 | 1/2007 |
| WO | WO2007/007058 * | 1/2007 |

OTHER PUBLICATIONS

Boston Scientific Medizintechnik GMBH, Invoice No. 7131891068, Oct. 23, 2013, 3 pages, Germany.

Boston Scientific Medizintechnik GMBH, Invoice No. 7131891070, Oct. 24, 2013, 4 pages, Germany.

Boston Scientific, Vercise Deep Brain Stimulation System Physician Manual, 75 pages.

Boston Scientific, Vercise Deep Brain Stimulation System Programming Manual, 91 pages.

Medtronic, Reclaim DBS Therapy of OCD—Lead Kit for Deep Brain Stimulation Implant manual, 79 pages.

Cleveland Clinic, Cleveland Clinic Performs Nation's First Deep Brain Stimulation for Stroke Recovery , Jan. 4, 2017, 5 pages.

* cited by examiner

SECTION A-A

METHOD AND DEVICE FOR DEEP BRAIN STIMULATION

CROSS REFERENCE TO RELATED APPLICATIONS

The present application claims the benefit of British Application Serial No. 1510781.6, filed Jun. 19, 2015, the disclosure of which is incorporated herein by reference in its entirety.

BACKGROUND

Therapeutic use of Deep Brain Stimulation (DBS) was first demonstrated in 1991 in the treatment of disabling tremor by Benabid, marking a clear step forward from brain ablative therapies. It has since been used successfully to treat various diseases of neural origin including Parkinson's disease, neuropathic pain and dystonia. It has also recently shown promise in the treatment of addiction and Obsessive Compulsive Disorder.

In general, DBS is considered to be a safe procedure and more than 10,000 patients covering a spectrum of indications receive implants every year with low risk of fatal or serious adverse events. According to comprehensive analysis of 10 years of literature by Zrinzo et al in 2012, the overall incidence of haemorrhage in functional neurosurgery (DBS and ablative) is 5.0%, 1.9% of these being asymptomatic. However, older age and hypertension (HT) were associated with an elevated risk of haemorrhage. In DBS, the use of image-guidance technology by Zrinzo et al. reduced the risk of haemorrhage to 0.9%. At North Bristol NHS Trust hospital (Bristol UK), where image-guidance technology is combined with a state-of-the-art neurosurgical, stereotactic robot, the risk has been reduced further to 0.3%. In comparison to ablative procedures, DBS has the advantage of being reversible in that the device can be turned off, or the electrode(s) removed. Additionally, it allows iterative optimisation of stimulation intensity, frequency and pulse width once implanted.

Despite relatively widespread use over recent years, the precise mechanism of DBS action is unclear. It is widely thought that the electrical stimulus controls the excitability of neurons (predominantly fibres, but cell body activation cannot be excluded) within close proximity of the implanted electrodes. Stimulus frequency is broadly used to excite (at approximately <40 Hz) or inhibit (at approximately >120 Hz) neurons; the stimulus amplitude and pulse width used provide control of the amount of charge applied to reach an empirically defined threshold. The threshold response is also determined by the physical proximity of the electrode contacts to the brain region/nucleus of interest. Electrodes have either four (Medtronic Inc) or eight (Boston Scientific Corp) circumferential contacts evenly distributed along the lead, which is connected to an implantable pulse generator (IPG) placed subclavically and enables either monopolar (with the IPG case acting as the anode) or bipolar (between contacts) stimluation configurations. Such flexibility gives scope for optimisation of the stimulation field within the target to titrate the beneficial response against any stimulation-induced side effects.

Periventricular Gray (PVG) and Periaqueductal Gray (PAG)

The periventricular gray (PVG) and periaqueductal gray (PAG) have been recognised as targets for deep brain stimulation (DBS) in the treatment of intractable pain since 1977. The PAG resides within the midbrain and its role in autonomic function has been studied extensively in animal models, where it was discovered to be critically involved in mediating the defence response. This response can be considered as 'survival instinct' as it stems from the autonomic response to perceived or present danger. Perceived escapable fear elicits a fight or flight response comprising a pattern of cardiovascular and respiratory changes including: hypertension, tachycardia, adrenaline release, increased blood flow to skeletal muscles and hyperventilation coupled with inhibition of the baroreceptor reflex and strong analgesia. In contrast, perceived inescapable fear, where it is advantageous to remain undetected, causes the opposite response pattern of freezing, the so called 'play dead' response consisting of hypotension, bradycardia and hypoventilation, and is also coupled with analgesia. Both responses are mediated from the PAG but from separate sites: the dorsal PAG produces the fight and flight response whereas the ventral portion produces the 'play dead' response. The association of the PAG with fear, pain modulation and autonomic function is also evident in humans.

We now understand that the PAG consists of four anatomically and functionally distinct, longitudinal columns defined by their position relative to the central aqueduct; the dorsomedial, dorsolateral, lateral (lPAG) and ventrolateral PAG (vlPAG). The vlPAG has dense projections to known cardiovascular integration sites within the CNS including medullary and hypothalamic nuclei in addition to those involved in motor control and analgesia. The vlPAG also receives projections from regions involved in somatosensory feedback and autonomic regulation including forebrain cortical structures, the limbic system, spinal afferents and hypothalamic nuclei. In addition, there is some evidence for intrinsic neuromodulation within the PAG via a web of anatomically identified interneurons.

Hypertension

Stimulation of the vlPAG elicits a depressor response and bradycardia mediated by inhibition of sympathetic premotor neurons in the rostral ventrolateral medulla in anaesthetized animals and this pathway is likely to involve a relay in the medullary raphe nuclei. However, this response is less pronounced or absent in conscious normotensive rats. The contribution of the PAG in the development of hypertension is unclear, although there is evidence to suggest the neuronal activity output from the dorsal PAG is elevated in the spontaneously hypertensive (SH) rat (Schenberg 1995)[1]. The role of the vlPAG in the cause and long-term control of HT in the SH rat has yet to be ascertained.

A putative role of the vlPAG in cardiac baroreflex sensitivity may involve inhibitory connections within the PAG since the lateral PAG projects to sympathetic preganglionic neurons to inhibit baroreflex bradycardia. Both electrical and excitatory chemical stimulation of the vlPAG have been shown to facilitate the arterial baroreflex response via projections to the raphe magnus nucleus in anesthetised normotensive rats. PAG input to the nucleus of the tractus solitarius (NTS) may provide the neural substrate for baroreflex modulation as well as modulation of somatic afferents including nociceptive inputs. Interestingly, stimulation of the dorsal and lateral PAG inhibits baroreflex bradycardia, partly via direct modulation of cardiac vagal preganglionics in the nucleus ambiguus and partly by modulation of sympathetic efferents by the lateral parabrachial nucleus. Chemical ablation of the dorsolateral PAG increases baroreflex tachycardia but does not affect reflex bradycardia, suggesting a tonic inhibitory role of the dorsal PAG in cardiac baroreflex control. Interestingly, 24 hours after lesioning the dorsolateral PAG both the cardiac baroreflex gain and mean arterial pressure (MAP) decreases in the SH rat. This counter-intuitive change in cardiac baroreflex gain suggests that the removal of tonic sympathoexcitatory activity predominates in the MAP response in the early stages after lesioning.

Ideally, a DBS Central Nervous System (CNS) target site for control of blood pressure should be easily accessible and reached safely with minimal risk of injury, trauma or haemorrhage. The electrode tract should not transverse across nuclei, major fibre tracts or blood vessels. When activated, the site should not cause adverse motor or behavioural responses, or unpleasant sensations, and must be without deleterious side effects. The site must be embedded in a neuronal network that can produce titratable falls in blood pressure through activation of neurohumoural mechanisms that should include resetting of the baroreceptor reflex to lower pressure levels and improve sensitivity. Ideally, a site that can reset the central set-point of arterial pressure would be also be most advantageous, and may occur and/or be assisted by resetting the baroreceptor reflex. All told, the connectome of the vlPAG appears to fulfil the above mentioned criteria.

The globally accepted diagnosis for treatment resistant HT is an office blood pressure measurement exceeding 140/90 mmHg whilst on pharmacological intervention with 3 or more anti-hypertensive medications (including a diuretic). Currently, there is some debate on the actual percentage of HT patients that meet the criteria for a diagnosis of resistant HT; reports range from 8.9% up to 16.4%. Current estimates based on an analysis of multiple global trials report up to 15% of HT patients can be classed as having resistant, essential HT. To put this figure into context, there are presently 0.9 billion patients worldwide with HT currently and >1.5 billion are predicted by 2025, making this one of the greatest healthcare burdens to patients and the economy. The prevalence of resistant HT suggests that existing pharmacological interventions have failed for many patients. This coupled with the fact that some drugs are poorly tolerated by patients, with associated non-adherence, suggests that there is a need for improved medical treatment.

Recently, a number of device based procedures have been studied and are being trialled worldwide. These procedures have had varying degrees of success in controlling blood pressure in the clinical trials completed to date. The devices trialled thus far have targeted the cardiovascular autonomic nervous system, which is considered to be a major driving force for development and maintenance of resistant HT. The most extensively studied of these is renal denervation (RDN), where ablation of the renal sympathetic nerves is achieved with a catheter emitting radio-frequency energy inserted peri-cutaneously into the renal artery (The Symplicity HTN-2 Trial 2010), making this a non-reversible procedure. The hypothesised mechanisms of action are: (i) reduction of hyperactive renal sympathetic drive to reduce vascular resistance, improve glomerular filtration rate and lower sodium/water re-absorption; and (ii) remove renal afferent activity thought to be predominantly sympathoexcitatory in reflex nature. Although high success rates were reported in the original Symplicity HTN-1 and HTN-2 trials, most experience indicates a persistent blood pressure reduction in 50% of drug resistant hypertensive patients (Hart 2013), which is consistent with that of other studies. Nevertheless, the most recent trial (Symplicity HTN3, Medtronic) failed to reach its endpoint of a reduction in office and ambulatory blood pressure.

While individuals with HT tend to have a reduced sensitivity to acute pain (hypoalgesia) a study of 10,135 Nordic subjects conducted by Olsen et al 2013 identified a 23% increased incidence of HT in the group with chronic pain. This suggests that there is linkage between dysfunction in cardiovascular and pain modulatory systems.

The antihypertensive effect of vlPAG DBS has been observed in patients receiving treatment for neuropathic pain that were also diagnosed with HT (Green 2005)[3], (Patel 2011)[4]. In one such patient, blood pressure could be increased and decreased acutely during surgery by stimulating either the dorsal or ventral PAG respectively, which reflects the responses observed in experimental animals. Chronic DBS of the vlPAG caused a reduction in arterial pressure and analgesia which are associated with changes in heart rate variability indicative of inhibition of sympathetic vasomotor tone and an increase in parasympathetic cardiac activity (Pereira, Lu 2010)[5], which led the authors to describe a "Method and apparatus for regulating blood pressure" WO 2007007058. Muscle sympathetic nerve activity was decreased in a patient during acute vlPAG DBS (Sverrisdottir 2014)[6]. In addition, the depressor and bradycardic effect of acute vlPAG DBS was coupled with an increase in baroreflex sensitivity. However, in these cases, the prevailing belief has been that the beneficial blood pressure effects were a secondary effect to the relief of chronic pain.

At North Bristol NHS Trust hospital (Bristol UK), we have observed striking responses in blood pressure reduction following DBS of the vlPAG. Using a robot for stereotactic positioning of the electrode with visual image-based confirmation of the position of a pre-inserted guide tube and stylette (Renishaw plc) (Patel 2007)[7], we have targeted the vlPAG reliably and with precision. In 2011, we reported the first case study where stimulation of the vlPAG alleviated neuropathic pain and, serendipitously, produced a sustained (>3 years) normalisation of arterial pressure that was not secondary to the relief from pain, as the patient's pain scores returned to pre-vlPAG stimulation levels after 4 months. The patient then had all antihypertensive medication withdrawn and was normotensive with midbrain stimulation alone. The patient continues to remain normotensive beyond 5 years whilst maintained on DBS and a single antihypertensive medication (perindopril).

Other targets and methods of modulating blood pressure by electrical stimulation have been developed over recent years. For example Mayberg "Brainstem and cerebellar modulation of cardiovascular response and disease" WO2004069328 describes a method of control of blood pressure employing electrodes in the brainstem. Gelfand et al, "Implantable device and method for treatment of hypertension" US20060041283, describes another method employing stimulation of peripheral nerves.

Alzheimer's Disease

Alzheimer's disease (AD) is the most common type of dementia, predicted to affect 1 in 85 people globally by 2050. The cause of Alzheimer's disease is largely unknown, but older age, family history and poor cardiovascular health are known to increase the risk of developing the condition.

An advantage of DBS is that memory structures can be accessed directly. In Lozano and Flaherty "Deep Brain Stimulation of Memory Circuits in Alzheimer's Disease"

US2013289385A1, an investigative procedure employing DBS of the fornix to treat Alzheimer's disease is described.

Early trial results demonstrated increased cerebral glucose metabolism, which was correlated with improved cognition in some patients after one year (Lyketsos 2012)[8]. Bilateral DBS of the hypothalamus and fornix has led to improved memory function (Hamani 2008)[9]. DBS of the fornix has been shown to stabilize memory function in AD patients demonstrated in tests such as the MMSE, ADAS—Cog, Free and Cued Selective Reminding Test (Fontaine 2013)[10]. High resolution positron emission tomography studies revealed a persistent fornix—DBS effect on cerebral metabolism in memory processing structures one year after stimulation that correlated with improved cognitive and memory functions (Smith 2012)[11].

DBS of the entorhinal cortex can induce phase resetting of hippocampal theta oscillations in humans. Theta resetting can enhance the encoding of new information and enhance memory. DBS of the entorhinal area thus seems to be a promising target in treating pathological AD to enhance memory functions. DBS may reduce memory dysfunction by promoting the physiological conditions and patterns of extracellular field potentials necessary for long-term memory. Furthermore, there is evidence in rodents that fornix and performant path stimulation increases hippocampal neurogenesis and long-term potentiation to facilitate memory storage (Hardenacke 2013)[12]. The nucleus basalis of Meynert (NBM) has several cholinergic projections which degenerate in AD, thus the NBM is a potential future target for DBS in AD. Another auspicious, but not yet investigated target of DBS in AD patients may be stimulation of the anterior thalamic nucleus, as prior to encoding, its stimulation has been observed to improve verbal memory in epileptic patients Whether bilateral or unilateral stimulation is more effective to enhance memory remains unresolved.

There appears to be a connection between hypertension and the dementia associated with Alzheimer's disease. De la Torre et al 2002[13] argues that there is a likely vascular element to the development of Alzheimer's disease and that one indicator is midlife hypertension. Hypoperfusion of the brain may play a role in the development of cognitive and memory impairment in Alzheimer's disease. Roher et al 2012[14] identified a 20% decrease in cerebral blood flow in a group of individuals with mild to moderate Alzheimer's disease (n=8) compared with those from a group of age-matched non-demented control subjects (n=9).

Patients with Alzheimer's disease also suffer from autonomic dysfunction, and a wide array of behavioural and cognitive problems. The PAG is involved in various autonomic, cognitive and behavioural processes, and has been shown to develop selective pathological changes in Alzheimer's disease (Parvizi 2000)[15].

As discussed above, many experts acknowledge a link between cerebral hypoperfusion and the risk of developing Alzheimer's disease. There remains debate as to whether decreased perfusion is symptomatic or causal but hypoperfusion is associated with structural changes in the brain and therefore treatments that address this may prevent or slow progression of the condition.

Multiple Sclerosis

Perfusion has also shown to be altered in multiple sclerosis. Gray matter exhibits globally reduced perfusion (Debernard 2014)[16] and cerebrovascular reactivity (Marshall 2014)[17] in patients when compared with controls, in the absence of volume loss, and consistent with neuronal metabolic dysfunction in early disease. Demyelinating cortical lesions show both significant reduction in cerebral blood flow and cerebral blood volume (Peruzzo 2013)[18].

Minimally Conscious State (MCS)

Reduction of cerebral blood flow (CBF) has been observed in MCS patents within the medial prefrontal and midfrontal cortical regions as well as gray matter (Liu 2011)[19] and improvements in blood flow correlate with clinical improvement. The central thalamus and specifically the centromedian parafascicular (CM-PF) nuclei have been stimulated to good effect (Yamamoto 2013)[20].

Mood Disorders

The PAG has a notable role in the processing of emotions and the regulation of mood, through its connections with the medial prefrontal cortical network and limbic system, including projections to the dorsomedial nucleus of the thalamus.

Epilepsy

Epileptic seizures result from excessive and uncontrolled desynchronisation of cortical nerve brain electrical activity, occurring in approximately 1% of world population and are controllable with medication only in about 70% of cases. In the remaining 30%, surgery or neuromodulation is an emerging treatment option.

In patients with medically refractory partial and secondarily generalized seizures, bilateral stimulation of the anterior nucleus has been demonstrated to reduce seizures by more than 50% over a 2-year period. Stimulation of the CM-PF has also been shown to be effective in the treatment of epilepsy.

Cerebro-Vascular Disorders

The protection of brain tissue in conditions that affect the small vessels resulting in ischaemic events poses a current challenge for critical neurological care world-wide, especially as there is no predictable efficacious treatment. Pathologies include small vessel disease which leads to vascular dementia; post-haemorrhagic vasospasm; and moyamoya disease.

Small Vessel Disease and Vascular Dementia

Vbascular dementia, the second most common cause of dementia beyond Alzheimer's disease, results from problems with blood supply to the brain. If the vessels are damaged, blood may not be able to reach the brain cells and consequently the cells may die of oxygen starvation triggering the onset of vascular dementia. Increasingly, it seems that one particular type of vascular disease, small vessel disease (SVD), may be the major form of vascular dementia.

Small vessel disease results from thickening of vessel walls, blood-brain barrier disturbance, demyelination and axon loss amongst other problems. The mechanism of SVD development is not clear, although there are two main pathological features. These are lesions of the subcortical, deep and periventricular white matter, generally referred to as white matter lesions and lacunes of the central grey matter, including the thalamus and basal ganglia.

The risk factors contributing to thickening of the blood vessel walls or atherosclerosis include hypertension and diabetes mellitus. The small arterioles are more susceptible to atherosclerosis as they are less elastic than the larger blood vessels. The thickening and hardening of vessel walls result in narrowing of the lumen of the vessel, twisting the vessel itself and thereby creating two conditions. The first is hypoperfusion whereby the supply of oxygen and nutrients to the brain tissue is slowly cut. The second condition is occlusion where blood supply to a particular part of the brain ceases. These conditions result in ischemic brain tissue.

There is a variety of experimental data illustrating that the progression of vascular dementia caused by SVD is continuous rather than stepwise. There is no established treatment for small vessel disease and vascular demntia, although the current approach focuses on treating risk factors for vascular disease. The strength of evidence for effectiveness of risk factor reduction is still not robust, although it may be more convincing for primary prevention of strokes and vascular dementia than for prevention of progression of existing vascular dementia. The benefit of lowering blood pressure and the blood pressure target are controversial. Although lowering blood pressure may prevent further strokes, those who have existing cerebrovascular disease may need higher blood pressure to maintain adequate cerebral perfusion.

Vasospasm

Alterations in CBF and metabolism after subarachnoid haemorrhage (SAH) are well known and have been extensively described. Cerebral vasospasm remains one of the most serious complications after SAH. This is the classic cause of delayed neurological deterioration after aneurysmal subarachnoid haemorrhage that leads to cerebral ischaemia and infarction with poor outcomes, and often death. Cerebral vasospasm consistently fails to respond to treatment, and there remains no efficacious treatment for this critical patient group. Radiologically, apparent vasospasm develops in approximately 60-70% of all patients with aneurysmal SAH. Of these cases, two thirds suffer clinical or symptomatic vasospasm with ischaemia sufficiently severe to cause transient or permanent neurological deficits. Vasospasm develops 3 to 14 days after SAH (peaking at 7 to 10 days) although the onset may be delayed up to 21 days.

Moyamoya Disease

Moyamoya disease is a rare, progressive cerebrovascular disorder caused by blocked arteries at the base of the brain in an area called the basal ganglia. The name "moyamoya" means "puff of smoke" in Japanese and describes the look of the tangle of tiny vessels formed to compensate for the blockage. Moyamoya disease was first described in Japan in the 1960s and it has since been found in individuals in the other countries around the world; its incidence is higher in Asian countries than in Europe or North America. The disease primarily affects children, but it can also occur in adults. In children, the first symptom of Moyamoya disease is often stroke, or recurrent transient ischemic attacks (TIA, commonly referred to as "mini-strokes"), frequently accompanied by muscular weakness or paralysis affecting one side of the body, or seizures. Adults may also experience these symptoms that arise from blocked arteries, but more often experience a hemorrhagic stroke due to bleeding from the abnormal brain vessels.

There are several types of surgery that can restore blood flow (revascularization) to the brain by opening narrowed blood vessels or by bypassing blocked arteries. Children usually respond better to revascularization surgery than adults, but with mixed results and at times high-risk, although the majority of individuals have no further strokes. Without surgery, the majority of individuals with Moyamoya disease will experience mental decline and multiple strokes because of the progressive narrowing of arteries. Without treatment, Moyamoya disease can be fatal as the result of intracerebral hemorrhage.

SUMMARY OF THE INVENTION

This invention concerns a device and a method of treatment by neuromodulation of the PAG either alone or in combination with other structures to increase brain perfusion and thereby treat disorders that are associated with compromised cerebral blood flow.

At its most general, the present invention proposes that a neuromodulation signal, such as an electrical pulse signal, is applied to the lPAG and/or vlPAG of a subject (patient). Such signals may then treat conditions such as Alzheimer's disease, Multiple Sclerosis, a Minimally Conscious State, Mood Disorders and/or vascular brain disorders where there is small vessel compromise, such as vascular dementia, small vessel disease, multiple stroke disease, post-haemorrhagic vasospastic disease and/or moyamoya disease, in the subject. Normally, before such treatment, it will already have been determined that the subject is suffering from one or more such conditions.

Normally, the signal is a low frequency signal, e.g. of 5 to 50 Hz. The present inventors have found that low frequency stimulation of the v1PAG results in a global increase in cerebral blood flow (CBF), cerebral blood volume and reduction in blood mean transit time.

Where the signal is an electrical pulsed signal, it is normally applied via a suitable electrode lead wire.

Thus, a first aspect of the present invention may provide a method of treating Alzheimer's Disease and/or Multiple Sclerosis and/or Minimally Conscious State and/or Mood Disorders and/or vascular brain disorders where there is small vessel compromise in a subject in need thereof; comprising: applying a neuromodulation signal to the lPAG and/or v1PAG of the subject.

The second aspect may provide a method of treating Alzheimer's Disease and/or Multiple Sclerosis and/or Minimally Conscious State and/or Mood Disorders and/or vascular brain disorders where there is small vessel compromise in a subject in need thereof, said subject having previously been diagnosed as suffering from Alzheimer's Disease and/or Multiple Sclerosis and/or Minimally Conscious State and/or Mood Disorders and/or vascular brain disorders where there is small vessel compromise, comprising applying a neuromodulation signal to the lPAG and/or v1PAG of the subject.

The third aspect may provide a method of treating Alzheimer's Disease and/or Multiple Sclerosis and/or Minimally Conscious State and/or Mood Disorders and/or vascular brain disorders where there is small vessel compromise in a subject in need thereof, comprising: selecting said subject for treatment based on a previous diagnosis for Alzheimer's Disease and for Multiple Sclerosis and/or Minimally Conscious State and/or Mood Disorders and/or vascular brain disorders where there is small vessel compromise in said subject, and applying a neuromodulation signal to the lPAG and/or v1PAG of the subject.

The method may be a method of treating vascular dementia and/or small vessel disease and/or multiple stroke disease and/or post-haemorrhagic vasospastic disease and/or moyamoya disease.

The neuromodulation signal may be an electrical pulsed signal. As has previously been mentioned, the application of electrical pulsed signals to a subject in situations other than those of the present invention has already been utilised. Nevertheless, other neuromodulation signals may be used. The use of optogenetic neuromodulation signals will be discussed later.

The electrical signal may be applied via an electrode lead wire. That wire may be implanted unilaterally into one hemisphere of the brain of the subject. In order to apply signals to the lPAG and/or vlPAG, the electrode should then preferably be implanted to a depth level with the superior colliculus of the subject.

The electrode lead wire may be externalised for a transient period of stimulation and/or connected to a RF-receiver buried in the skull and/or connected to a pulse-generator implanted in the skull.

In a development of the present invention, it has also been found that the treatment may be improved by applying further neuromodulation signals such as electrical pulse signals or light signals (in the case optogenetic methods) to the medial thalamus and/or fornix and/or anterior nucleus and/or the CM PF nuclei of the brain of the subject. That signal is preferably a high-frequency signal, of e.g. greater than 70 Hz.

In the case of structures such as the fornix, neuromodulation signals may be applied by placement of electrode(s) beside or overlying the structure rather than penetrating it as damage to the fornix may result and impair formation and recall of memories. In contrast, in the case of the PAG it is permissible to implant the electrode into the structure without undue damage.

The high and low frequency signals may be applied by different electrodes, but preferably a single electrode wire is inserted so as to traverse the medical thalamus and/or fornix and/or anterior nucleus, and extend to a depth level with the superior colliculus, with the electrode lead wire then being used to apply the different pulse signals to the respective parts of the brain of the subject.

Such an arrangement involving multiple signals with high and low frequency has also been found as suitable for treating Hypertension and/or Epilepsy, in addition to the conditions referred to earlier.

Thus, a further aspect of the invention may be a method of treating Hypertension and/or Epilepsy in a subject in need thereof, said subject having previously been diagnosed as suffering from Hypertension and/or Epilepsy, the method comprising:

applying an neuromodulation signal to the lPAG or vlPAG of the subject, wherein said electrical pulsed signal is a low frequency signal; and applying a further neuromodulation signal to the medial thalamus and/or fornix and/or anterior nucleus and/or the centromedian parafascicular nuclei of the brain of the subject, said further neuromodulation signal being a high frequency signal.

It is preferable to achieve the present invention by application to signals to only one hemisphere of the brain as this minimises surgical time and risk of complications such as haemorrhage. However in some cases clinical outcome may be improved by applying the signals to both hemispheres. In that case, electrodes may be implanted into both hemispheres, to a depth level with the superior colliculus of each hemisphere. Signals may then be applied to each electrode, either a low frequency signal, or both low and high frequency signals as previously described.

The discussion above has been concerned with the way the subject may be treated. The present invention may also provide, in a further aspect, an apparatus having two electrode regions separated along an electrode lead wire, with electrical pulsed signals being applied to those first and second regions, one having a high frequency signal and one having a low frequency signal.

Thus, this aspect may provide an apparatus for treating Alzheimer's Disease and/or for Multiple Sclerosis and/or Minimally Conscious State and/or Mood Disorders and/or vascular brain disorders where there is small vessel compromise and/or Hypertension and/or Epilepsy in a subject in need thereof, comprising a first electrode region and a second electrode region, the first and second electrode regions each having at least one electrode and being separated along an electrode lead wire with the centres of the electrode regions being 10 to 20 mm apart, and a controller for applying first and second electrical pulsed signals to said first and second electrode regions with respectively, the first electrical pulsed signal being a low frequency signal and the second electrical pulsed signal being a high frequency signal wherein the first electrode region is at the distal end of the lead and the second electrode region is proximal to the controller.

The centres of the electrode regions may be closer together than mentioned above, so that the lower limit of their separation may be 12 mm and the upper limit 17.5 mm. In either case, the electrode region should be separated so that, when the electrode lead wire is implanted into the subject, the electrode regions can be aligned with their respective targets in the lPAG and/or vlPAG and in the medial thalamus and/or fornix and/or anterior nucleus and/or CM PF.

The electrode region must have at least one electrode, and preferably has more than one. At least one of the electrodes may be split into multiple parts arranged around the electrode lead wire, with e.g. insulating material there between. There may also be insulating material between the electrode regions.

For example, the two electrode regions may each comprise three or more, preferably four, rows of ring electrodes arranged along the longitudinal axis of the electrode lead wire, with each ring electrode being split into two semi-circular segments separated by an insulating gap. Each electrode then has its own electrical connection to the controller, which may be in the form of an implantable pulse generator. In such an arrangement, it is preferable that successive ring electrodes are arranged so that the insulating gap of one ring electrode is circumferentially displaced by 90° relative to the insulating gap of the or each adjacent ring electrode.

In any of the aspects of the invention discussed above, the electrical pulse signal may provide neuromodulation, either continuous or in bursts or cycles, or even by optogenetic methods.

In the case of Hypertension, we have identified that in some patients continuous stimulation appears to block the natural diurnal rhythm in which blood pressure naturally falls at night. In these patients, cyclic stimulation whereby stimulation is applied only during the daytime and switched off at night restores the diurnal rhythm, reducing blood pressure day and night.

In the case of optogenetic neuromodulation, light is used to activate target neurons which have been genetically modified to make them light sensitive, for example by introducing viral vectors into the target regions. The neuromodulation signal may then be triggered by a light source, preferably an optical fibre. Again, such an arrangement may involve the optical fibre having active regions to trigger different parts of the brain.

The advantage of such an optogenetic method is that light sensitive proteins such as rhodopsins may be transvected to specifically target the neuronal types of interest. Optogenetic neuromodulation signals may be combined with high frequency signals, either optical or electrical, to suppress activity in brain targets other than the PAG, such as the medial thalamus, anterior nucleus, or fornix.

Optogenetic activation of target neurons which have been genetically modified to make them light sensitive may be provided by an optical fibre as previously mentioned. That optical fibre may have two active regions separated by a gap of 10 or 12 or 15 or 17.5 or 20 mm so that the active regions may be aligned with their respective targets.

FIGURES

FIG. 3 shows the change in blood flow across particular regions of the brain when PAG stimulation is switched on.

DESCRIPTION

We implanted a case series of five patients with electrodes implanted unilaterally into the v1PAG for chronic neuropathic pain using magnetic resonance image directed localisation (Patel et al., unpublished data). Three of these patients also had electrodes implanted into ventromedian/parafascicular complex (CMPf) and one into the ventro-posteriolateral nucleus of the thalamus. Neuromodulation of the v1PAG employed a low frequency signal of frequency of between 5 and 10 Hz, forward pulse width 90 to 180 microseconds and amplitude 1 V to 4.3 V. In all cases a balanced biphasic waveform was employed with zero net charge flow. Blood flow across the brain was measured through functional imaging of the rate of uptake of a C-11 diprenorphine tracer into tissue (KO using Positron emission tomography (PET).

Unilateral PAG-DBS resulted in bilaterally increased blood flow to the whole brain; no lateralised effect was noted. In response to the suggestion that this finding may be a consequence of the methodology, baseline measures of 3 healthy volunteers undergoing PET scanning (using the same process) did not show increased blood flow. In fact, the difference in whole brain blood flow between DBS patients and healthy volunteers approached significance in this small sample. In any case, an increase in mean arterial pressure should not alter cerebral blood flow, which would be maintained by autoregulation.

Figure 1:
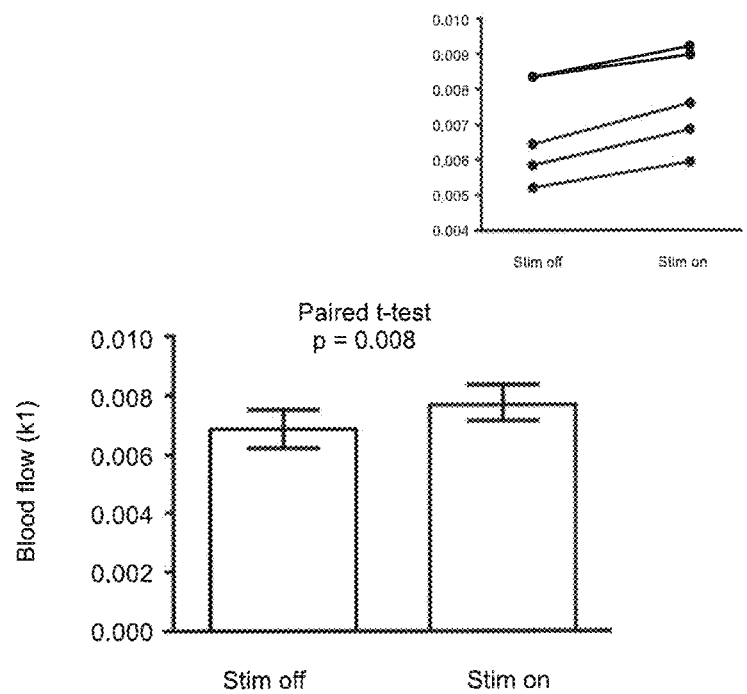
FIG. 1 shows the blood flow response in the electrode side of the brain with low frequency PAG stimulation applied unilaterally measured using a C-11 diprenorphine tracer in five subjects.

FIG. 1 shows the blood flow response to neuromodulation of v1PAG in the hemisphere of the brain in which the electrode was implanted. With stimulation turned on, all subjects exhibited an increase in brain perfusion throughout the hemisphere. Averaged over five DBS subjects, the increase in blood perfusion between stimulation on and off was just less than 14% (p=0.001).

Figure 2:
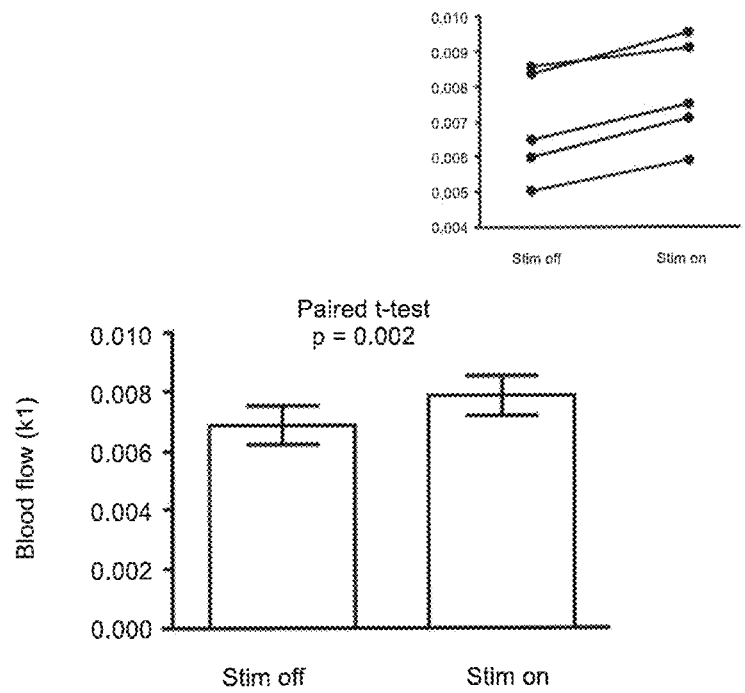
FIG. 2 shows the blood flow response in the non-electrode side of the brain with low frequency PAG stimulation applied to the contralateral hemisphere.

FIG. 2 shows the blood flow response in the non-electrode hemisphere of the brain. It is interesting to note that perfusion in the non-electrode hemisphere also increased by a similar amount (circa 14%) when v1PAG stimulation was switched on in the contralateral hemisphere.

Unilateral PAG-DBS resulted in significant bilateral increased blood flow to the PAG and anterior cingulate cortex. Again, no lateralised signature was seen. This is in keeping with the contralateral projection fibres within the PAG and the spread of electrical stimulation beyond the electrode tip. Consequently, we would expect PAG to exert its analgesic effect on both the contralateral and ipsilateral sides of the body, which has been described previously (Levy et al, 1987)[21].

Figure 3:
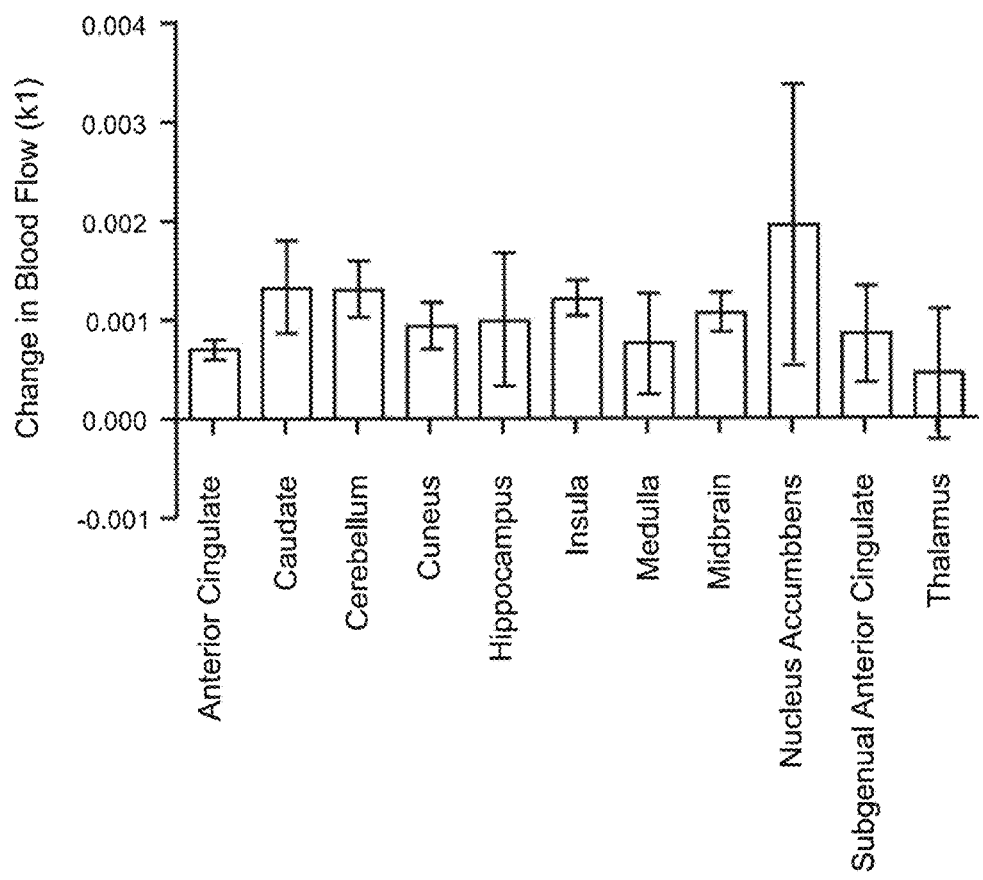

Referring to FIG. 3, other regions demonstrated non-significant increases in blood flow in response to PAG-DBS, namely the nucleus accumbens, subgenual anterior cingulate, hippocampus, insula, caudate, cerebellum, and the occipital lobe, with 10-15% increases in blood flow in these structures; although it is of interest to note that blood flow did not increase in the thalamus.

This increase in brain perfusion may be responsible for the known anti-hypertensive effect of v1PAG modulation. Increased blood flow within the brainstem may be expected to result in a centrally-driven and sympathetically-mediated decrease in blood pressure to autoregulate brain perfusion and reduced demands on the heart.

We believe that the 1PAG may also be an effective target for increase in brain perfusion, either alone or in combination with the v1PAG. In reality, the current path around the electrode site tends to be dispersed and therefore it is unlikely that these two structures can be exclusively targeted.

One aspect of this invention is therefore neuromodulation of the 1PAG and/or v1PAG as a treatment for early and late stage Alzheimer's disease, with a method that involves unilateral neuromodulation of the 1PAG and/or v1PAG resulting in increased perfusion across the entire brain. Unilateral stimulation of the right hemisphere would be preferred for Alzheimer's disease, as this is implicated in affective, cognitive function and memory storage in the majority of patients; and is non-dominant for speech function.

Neuromodulation of the PAG may provide a treatment for neurological conditions other than Alzheimer's disease, for example in multiple sclerosis autonomic dysfunction and perfusion disturbances globally and within cortical demyelinating plaques are well documented, and would likely benefit from PAG stimulation.

Neuromodulation of the PAG may also be combined with other targets. The dorsomedial nucleus of thalamus along with the midline nuclei act as a relay for inputs from a number of brain areas such as the solitary nucleus, substantia nigra reticulata, amygdala and ventral pallidum. The dorsomedial nucleus projects to the prefrontal cortex and the limbic system which is associated with attention, motivation, formation of long-term memory and sense of smell. The medial dorsal nuclei are also involved in processing pain. Neuromodulation of the dorsomedial nucleus may therefore be used to alter emotional response and memory. High frequency modulation of the dorsomedial nucleus and/or anterior nucleus may serve to improve memory formation.

Therefore, another aspect of this invention is combined neuromodulation of the lPAG and/or vlPAG and dorsomedial nucleus and/or midline nuclei as a treatment for early and late stage Alzheimer's disease. In combination, simultaneous low frequency modulation of the lPAG and/or vlPAG and high frequency neuromodulation of the dorsomedial nucleus and/or midline nuclei will serve to increase perfusion of the hippocampus and other important structures involved in cognition and memory.

These two targets may be addressed by implanting two electrode lead wires unilaterally, one targeting the lPAG and/or vlPAG and the other the dorsomedial nucleus and/or midline nuclei. Localisation may be achieved by any of the known methods for targeting deep brain stimulation electrodes, but image guided implantation is preferred. More preferably, according to this invention, a single electrode lead-wire is used to address both targets, so as to minimise both surgical time and risk employing image based guidance to accurately target both centres with the single lead.

Figure 4:
FIG. 4 shows an MRI scan of a typical straight-line trajectory with the electrode spanning the two targets of the medial thalamus and the PAG.

The medial surface of the thalamus forms the upper part of the lateral wall of the third ventricle. The preferred straight-line trajectory for an electrode lead-wire that encompasses both the medial thalamus and the PAG has an entry point in the frontal-parietal region of the skull and a trajectory that traverses the ventricle. FIG. 4 is a MRI scan of a section of the brain showing a straight line trajectory of an electrode, 41, traversing the medial thalamus proximally and the PAG distally. Optionally, a permanently implanted catheter may be used as a guide tube for the electrodes to assist the transventricular approach, such as that described by Gill in "A neurosurgical guide device" GB2357700B.

Figure 5:
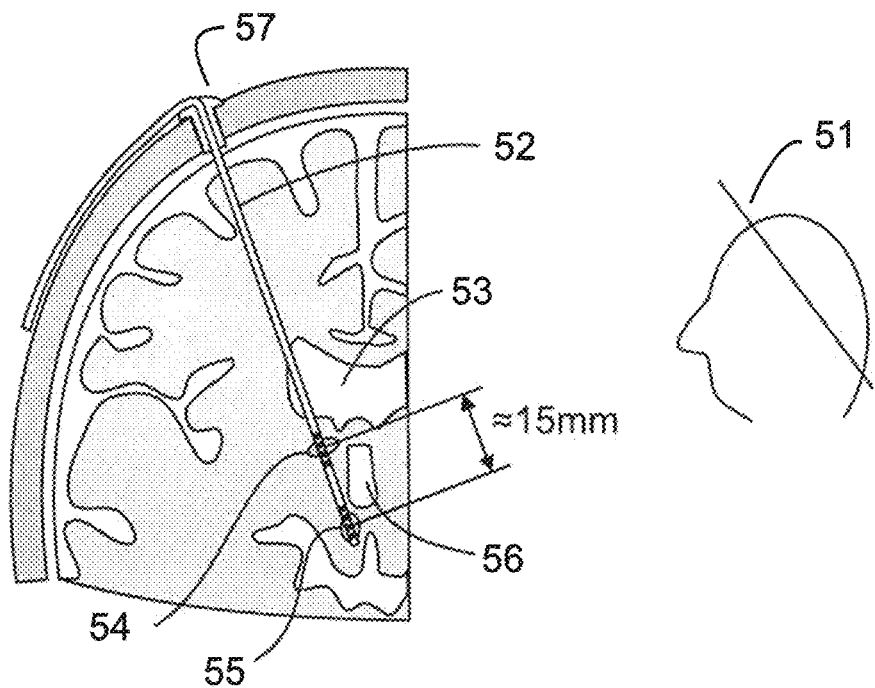
FIG. 5 is an illustration highlighting the key structures in FIG. 4.

FIG. 5 is an illustration that identifies the key structures involved. FIGS. 4 and 5 are slices at an angle through the head indicated by the cross section line 51. The lead, 52, follows a straight line trajectory from the burr hole and optional cap, 57, through the lateral ventricle, 53, into the medial thalamus, 54, bypassing the third ventricle, 56 into the PAG, 55.

According to this invention, high frequency modulation is applied to the medial thalamus to inhibit neurons in structures such as the dorsomedial nucleus, anterior nucleus and centromedian/parafascicular complex. This inhibitory high frequency modulation is a train of pulses of forward pulse width 25 to 350 microseconds, more preferably 60 to 90 microseconds, at a repetition frequency of greater than 70 Hz, more preferably in the range 100 to 200 Hz, or 130 or 150 Hz. The forward (negative going) pulses are delivered at amplitude of typically 1 or 2 to 3 or 5 mA with a current controlled output or 1 to 3 V with a voltage controlled output with a balancing reverse charge typically delivered at the same or lower intensity.

Also according to this invention, low frequency modulation is applied to the lPAG and/or vlPAG. Low frequency modulation consists of a train of pulses of forward pulse width 50 to 450 microseconds, at a repetition frequency of 5 or 10 to 40 or 50 Hz, typically 90 to 180 microsecond pulses of 1 or 2 to 3 or 5 mA amplitude with a current controlled output, or 1 to 5 V amplitude with a voltage controlled output. As before, a balancing reverse charge is required. Preferably the repetition frequency is 5 to 10 Hz or 20 Hz, however in some instances response is maximised at 40 Hz. This stimulatory low frequency modulation acts to excite neuronal activity in the lPAG and/or vlPAG.

A further aspect of this invention is optimization of the relative intensity of the high and low frequency modulation and the frequency of each modulation within their respective bands to optimise therapy; these are applied either continuously or in bursts, the latter which may be more physiologically representative.

Separation between the centres of the two targets varies, but is typically 15 mm as illustrated in FIG. 5. One aspect of the device is that the distal end of the electrode lead-wire should comprise two regions of active electrodes separated by a gap between the centre of each region of 10 or 12 or 15 or 17.5 or 20 mm. This ensures that the two regions of active electrodes are approximately aligned with the respective targets. The upper region of active electrodes (proximal electrodes) is aligned with the target in the medial thalamus. The lower region of active electrodes (distal electrodes) is aligned with the lPAG or vlPAG.

The respective high and low frequency modulation pulse trains are typically interlaced and applied to the proximal and distal electrodes. If electrical neuromodulation is used, preferably, the two pulse trains should be applied in a manner that ensures that there is no risk of cross flow of currents flowing between electrodes in the high and low frequency regions of the active electrodes.

This can be achieved by two means: (i) The output circuit is configured such that the output circuits in the implantable pulse generator (IPG) for the high and low frequency modulation are provided with galvanic isolation from each other by means of transformer or capacitive coupling between the power supply and output circuits. (ii) A contention circuit is provided in the implantable pulse generator (IPG) that ensures that the pulses in the high and low frequency modulation do not overlap in time. The contention circuit reschedules the output of one of the contending pulses until the other contending pulse has completed. Preferably pulses comprising the high frequency modulation are prioritised over those comprising the low frequency modulation so that the relative jitter on the pulse trains is minimised as a percentage of the overall mark-space ration of the pulse train.

Also according to this invention, using a single electrode lead wire of the type disclosed lPAG and/or vlPAG modulation may be combined with other targets associated with memory such as the fornix, provided a trajectory can be located that encompasses both the proximal target associated with memory and cognition and the distal lPAG and/or vlPAG.

Preferably, accurate positioning of the electrode lead-wire to address both targets with a single electrode lead wire is aided by Magnetic resonance imaging (MRI) guidance, optionally with Diffusion tensor imaging (DTI) to provide visualization of the neural tracts. Even with the benefit of this technique, lead placement may be optimised after implantation by sensing of local field potentials (LFPs) in order to identify the target accurately. The characteristic LFP rhythms that can be employed for targeting vary by condition, for example AD and depression tend to be associated with theta and delta rhythms in the medial thalamus respectively.

Additionally, it may be desirable to exclude certain stimulation locations and directions, in particular those associated with visual sensory feedback by looking for saccade-related (eye movement) LFPs which will assist confirmation of depth within the PAG and enable choice of optimal contact/s above this zone whilst avoiding any eye-related side-effect. The risk of anxiety as a side-effect may be reduced by avoiding lateral and dorsal directions. In order to facilitate this, a lead with directional capability may be desirable.

In summary, one aspect of this invention is a device and a method of treatment of Alzheimer's disease utilising dual frequency/dual target neuromodulation with a single lead implanted traversing the medial thalamus or the fornix into the lPAG and/or vlPAG to a depth level with the superior colliculus with high and low frequency modulation applied to the respective targets.

In the treatment of hypertension using low frequency DBS of the lPAG and/or vlPAG, an increase in repetition frequency from typically 5 to 40 Hz and increase in amplitude of the applied stimulus produces a corresponding greater reduction in resting blood pressure. However, an increase in frequency or amplitude may be associated with side effects caused by leakage of current to nearby structures, such as anxiety. With dual target stimulation of the medial thalamus and PAG using a single lead adapted to modulate both targets, high frequency modulation of the medial thalamus may be used to suppress the emotional response generated by leakage of low frequency currents from the region of the lPAG and/or vlPAG.

In non-hypertensive subjects modulation of the lPAG and/or vlPAG does not materially affect resting blood pressure because these individuals do not exhibit increased sympathetic activity in the resting state.

Preferably the electrode lead-wire should be implanted unilaterally and in the non-dominant hemisphere of the brain. The non-dominant hemisphere is normally the right side, contralateral to the side that primarily controls speech processing.

In respect of pain, preclinical data demonstrates the role of the parafascicular complex in the medial thalamus in nociception (Shi et al 2011)[22]. The dorsomedial nucleus and the centromedian/parafascicular complex are in close proximity, with the dorsomedial nucleus promixal to the entry point using the transventricular trajectory contemplated in this invention. This allows the proximal electrodes in the electrode lead-wire described herein to modulate either the dorsomedial nucleus or centromedian/parafascicular complex, or both. The electrode lead-wire is preferably implanted in the hemisphere contralateral to the site of pain.

A case series of four subjects were implanted at North Bristol NHS trust with the PVG/PAG modulated at 10 Hz and the dorsomedial nucleus and/or centromedian/parafascicular complex modulated at 132 Hz. Modulation of the PAG produced a sensation of warmth, a reduction in cold pain threshold and 70% reduction in pain. Modulation of the dorsomedial nucleus/centromedian/parafascicular complex resulted in paraesthesia (a tingling sensation) over the painful region, an 80% reduction in pain and reported telescoping of phantom limb. Modulation of both targets simultaneously produced a greater reduction in allodynia scores and overall pain score than individual targets alone. The mechanism of action is not fully elucidated but may be that PAG modulation gates noxious stimuli via descending opioid projection, while also projecting to supratentorial structures. Parafascicular complex stimulation modulates sensory input via the thalamus and projects to the nucleus accumbens causing a reported sensation of dissociation from the pain in subjects.

Therefore, also according to this invention low frequency modulation of the PVG/PAG at less than 40 Hz or 50 Hz and high frequency modulation of the dorsomedial nucleus and/or centromedian/parafascicular complex at greater than 70 Hz, 80 Hz, 90 Hz, 100 Hz or 130 Hz may be employed using either two electrodes implanted unilaterally or a single electrode adapted for dual target stimulation also implanted unilaterally.

In two patients implanted with electrodes in the dorsomedial nucleus and vlPAG, modulation of the vlPAG produced an immediate reduction in anxiety. As discussed, modulation of the dorsomedial nucleus is implicated in emotional response and therefore combination of the two targets is a promising treatment for medically refractory depression employing a single electrode implanted unilaterally in the right hemisphere of the brain. The PET blood flow results disclosed above further augments this theory with increased perfusion observed in the subgenual cingulate gyrus, dorsal cingulate gyrus, nucleus accumbens, amygdala and insula.

A short form Profile of Mood States (POMS-SF) developed by Shacham (1983) was used to assess mood changes in the case series of five patients at North Bristol NHS trust with PAG stimulation on and off. Table 1 summarises these results. Significance was tested using a two tailed paired t-test, improvement in all mood scores from PAG stimulation was observed. While changes in subset scores other than Anxiety were not significant in this small case series, the total POMS results indicates a substantial and significant improvement associated with PAG stimulation.

TABLE 1

| POMS Subset Score | % change with DBS on | p |
|---|---|---|
| Anxiety | −45.0% | 0.001 |
| Depression | −14.3% | 0.37 |
| Anger | −11.1% | 0.37 |
| Vigour | +20.7% | 0.30 |
| Fatigue | −48.4% | 0.10 |
| Confusion | −46.7% | 0.08 |
| Total POMS | −73.6% | 0.008 |

Depression is associated with functional insufficiency of the right hemisphere combined with its physiological overactivation, such that unilateral right PAG stimulation would be preferred, especially with PET blood flow results showing increased ipsilateral perfusion within the subgenual cingulate, amygdala and insula, and bilaterally in the nucleus accumbens.

Patients often present with combined hypertensive and chronic pain syndromes. As observed by Olsen et al 2013, these conditions may be linked. A case series of three patients with pain and hypertension were implanted with dual stimulation in the medial thalamus and vlPAG. In all cases, a reduction in resting blood pressure, pain and anxiety has been observed; a 'virtuous circle' in which reduction in pain and anxiety may lead to further reduced in blood pressure. With the electrode lead-wire described in this invention, a single unilateral procedure may be employed to treat the condition, minimising cost, surgical time and risk to the patient.

There are other neurological conditions in which dual target stimulation of the thalamus and PAG may be effective. For example persistent vegetative and minimally conscious states (disorders of consciousness) may be treated by a method comprising dual target stimulation of the medial thalamus and the PAG, which may prove to be more beneficial than stimulation of a single target alone.

In the treatment of epilepsy, stimulation of dual targets unilaterally or bilaterally with combinations including the anterior nucleus and CM-PF, or anterior nucleus and PAG, or CM-PF and PAG may produce a generalised cortical synchronisation, reducing the abnormal cortical excitability that underlies epilepsy. Stimulation may be provided continuously, intermittently or in response to sensed abnormality in cortical activity.

Electrode Lead Configuration

If PAG stimulation only is required typically four contacts are sufficient to provide coverage of the target while providing adjustment to compensate for positional deviation from the target along the axis of the lead. Such electrode lead wires are in common use in DBS surgery and consist a cylindrical electrode lead wire of typically 1.3 mm diameter with four cylindrical contacts at the distal end each of between 1 to 3 mm in length separated by gaps of 0.5 to 2 mm.

A directional electrode lead may be preferred in order to provide a degree of radial selectivity to more accurately focus stimulation towards the target in the case of lateral displacement of the lead from the desired target. Directional electrodes are desirable in order to optimise therapy delivery while minimising disturbance of nearby nuclei and fibre tracts, potentially reducing side effects. Certain types of directional electrodes are known in the art as described by Hegland et al "Implantable lead with multiple electrode configurations" US20080269854 and Moffitt et al "Deep brain stimulation current steering with split electrodes" US20100268298.

For dual targets addressed by a single non-directional electrode lead wire as contemplated in this invention, two active regions each of typically four contacts are provided, separated by a gap so that the active regions are located with their centres separated so that the active regions are approximately aligned with the two targets. For a combination of medical thalamus and PAG neuromodulation as previously described, separation varies by individual but is approximately 15 to 20 mm.

Figure 6:
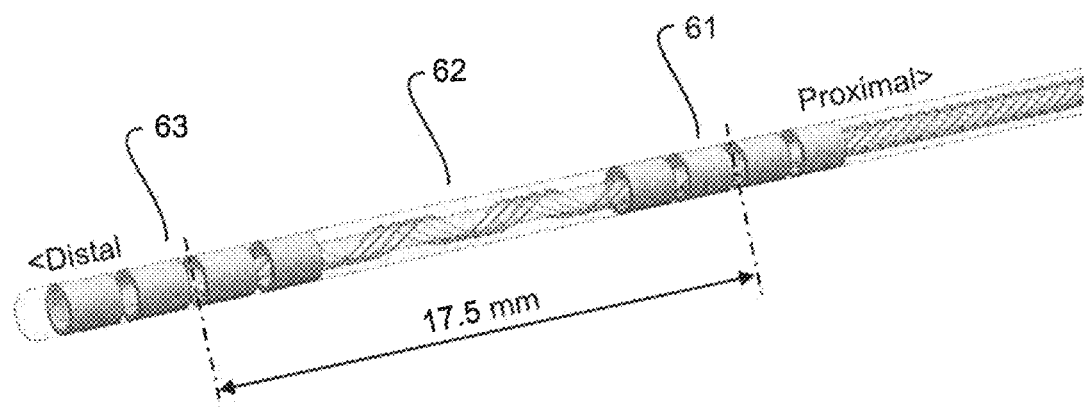
FIG. 6 shows an electrode lead wire adapted for dual target stimulation comprising two active regions of electrodes which are approximately aligned with the two targets.

An electrode lead adapted as described is illustrated in FIG. 6. The lead at its distal end comprises a group of four cylindrical electrodes (63) separated by a gap (62) and four cylindrical electrodes at the proximal end (61). In this embodiment the separation between proximal and distal electrode groups is 17.5 mm between centres and the electrodes are 1.5 mm in length separated by insulated gaps of 0.5 mm. Accordingly the lead illustrated is suitable for stimulating targets which are separated by 11.5 to 23.5 mm between centres.

Variation of electrode pitch/gap and separation between targets may dictate the use of other separation between distal and proximal electrode groups, but typically the range is 5 to 30 mm, more preferably 8, 10, 15, 20 or 25 mm. Four electrodes in each electrode group are normally sufficient, but any number from one upwards may be employed.

Figure 7:
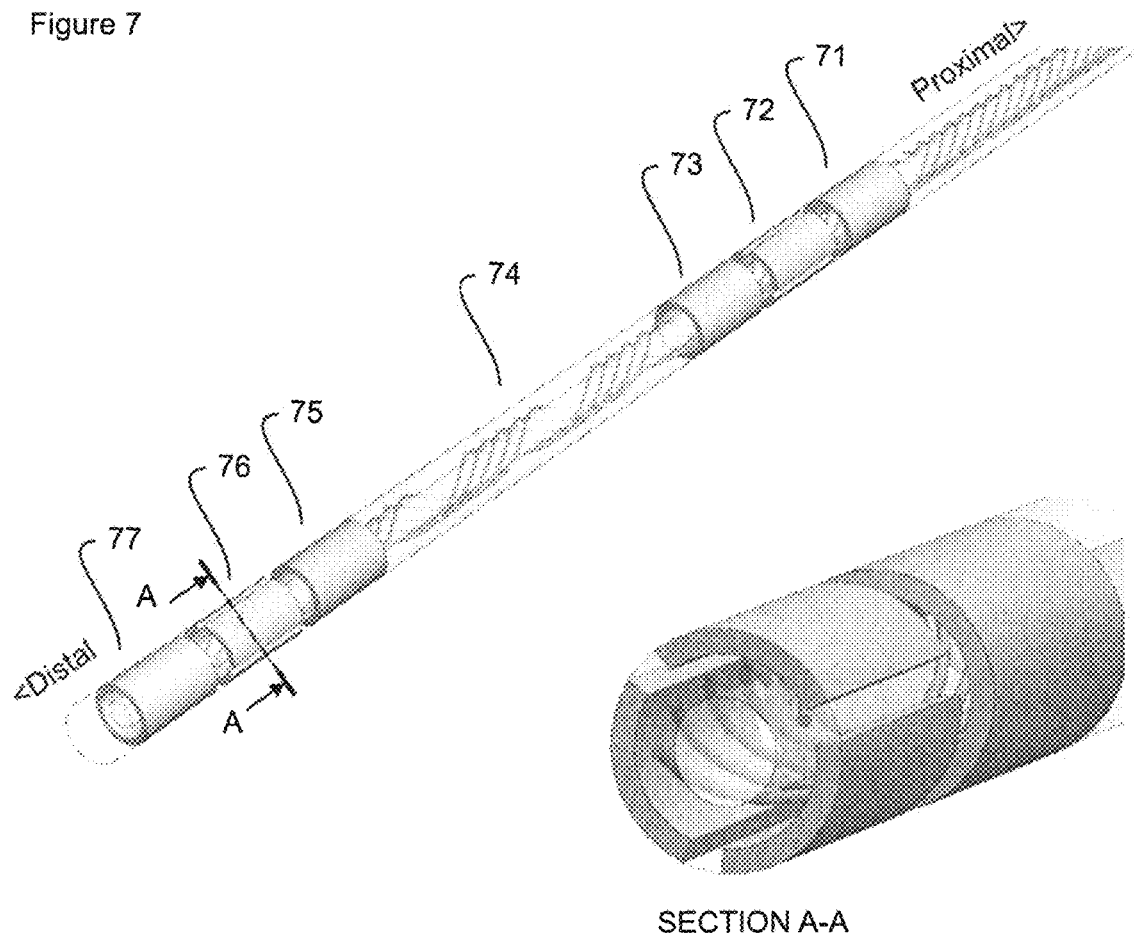
FIG. 7 illustrates an arrangement of a directional lead according to this invention that has three ring electrodes at proximal and distal electrode groups in which the central ring electrodes are divided into three segments to provide radial directionality.

FIG. 7 illustrates an arrangement of a directional lead according to this invention. The lead comprises three cylindrical electrodes in the proximal (71,72,73) and distal (75, 75,76) electrode groups separated by an insulated separator (74). In this embodiment the centre electrode of each electrode group is split into three radial segments each covering an arc of 100 degrees with a 20 degree insulator between each segment. The arrangement of the segmented annular electrode is shown by section A-A of FIG. 7.

Ideally a directional lead should have the minimum number of controllable electrodes consistent with achieving the desired level of directionality. The reasons for this are that fewer electrodes minimizes the number of wires in the lead and minimizes the complexity of the connection between lead and IPG and the hermetic feed-through in the IPG itself. Perhaps most important, there is a minimum electrode area for a particular forward (typically negative going) charge level at which the metal species in the electrode do not migrate into the tissues, above which there are risks of long term electrode decomposition and toxicity. This consideration favours directional leads with fewer, larger electrodes.

The lead illustrated in FIG. 7 provides translation of the electrical field both in radial and axial directions at each of the distal and proximal groups. This translation is provided by selecting the appropriate electrode to act as cathode in an electrode pair consisting of a cathode and one or more anodes.

Conventionally, electrical neuromodulation employs a negative pulse of desired pulse width and current or voltage applied to the cathode, followed by a balancing reverse charge to ensure that the net charge delivery is zero. In combination with the pulse charge limit mentioned above, zero net charge is important to ensure that ionic species generated at the electrode tissue interface during delivery of the forward charge are recombine during the reverse charge. This balancing charge is typically delivered at the same or lower current or voltage than the forward charge, either by means of an active recharge at a lower current for a proportionally longer duration as required or by discharge of series capacitors in the output circuit. In the electrode lead in FIG. 7, radial control is provided by always recruiting the central electrode as either anode or cathode. For example, in the case where one of the outer of the three electrodes is cathode, selection of one of the three central radial contacts will cause current to tend to flow in the tissues on that side of the electrode.

The lead arrangement in FIG. 7 has the advantage that it requires only ten connections to the IPG. A further saving in connections can be made by connecting the outer ring electrodes 73+75 in parallel, similarly with 71+77 (or 77+73 and 75+71), multiplexing the electrodes. This reduces the overall number of connections to the IPG to just eight. In practice, with such a multiplexed arrangement there is some cross leakage of current between shared electrodes but this is minimal because of the close proximity of the nearby anodes and cathodes in each electrode group ensures that there is lower resistance between electrodes in each group and therefore the majority of current flows within the group.

Further refinement of the applied electrical field to improve control of the effective point at which neuromodulation is delivered to the tissues both in non-directional and directional electrodes described herein may be obtained by modulating the pulses applied to multiple electrodes as described by Gillbe in "Array Stimulator" U.S. Pat. No. 8,612,018 B2, or by sharing current between the electrode using multiple current sources as described by Woods et al "Implantable generator having current steering means" U.S. Pat. No. 6,909,917 B2.

Figure 8:
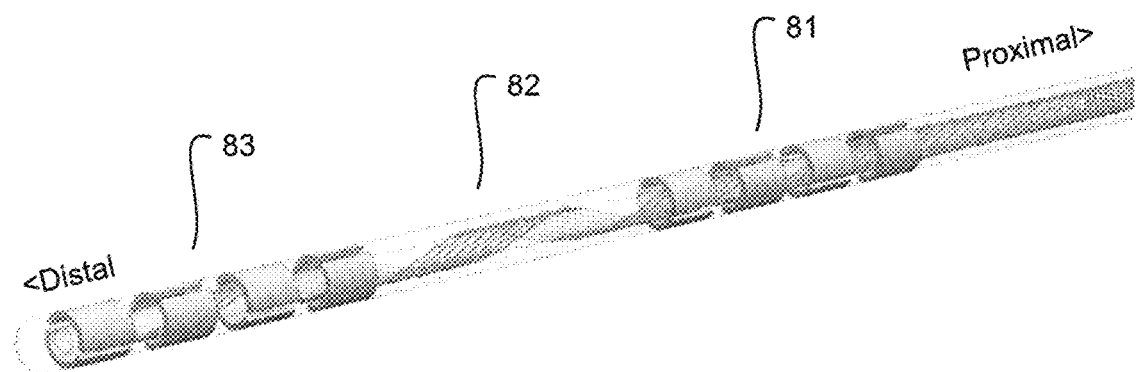
FIG. 8 illustrates an alternative arrangement of a directional lead in which the distal and proximal electrode groups each consist of four rows of semi-circular ring electrodes.

An alternative arrangement of segmented electrodes in presented in FIG. 8. In this example the distal and proximal electrode groups each consist of four rows of semi-circular cylindrical electrodes (81, 83), each covering a 180 degree arc, separated by a gap 83. This arrangement requires sixteen connections to the IPG if no electrodes are multiplexed. A variation of this arrangement, consisting of three rows of segmented electrodes requires 12 connections to the IPG.

Figure 9:
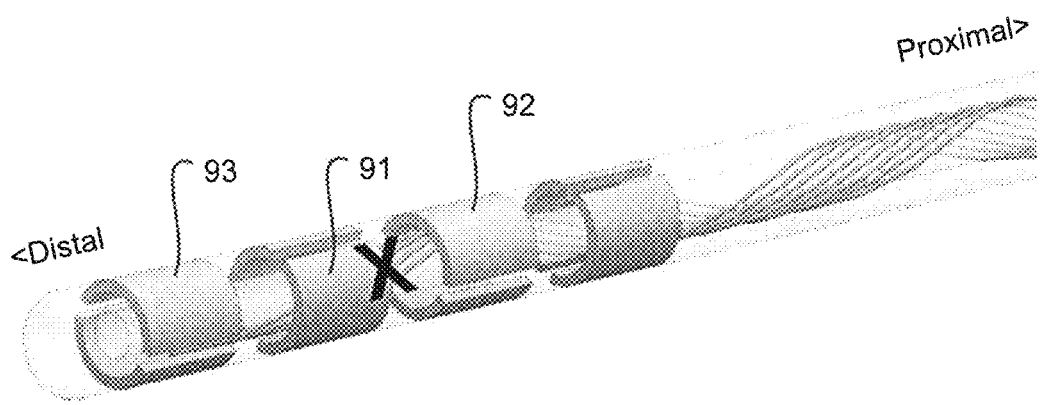
FIG. 9 is an enlargement of part of the electrical lead wire illustrated in FIG. 8.

The distal group is presented enlarged in FIG. 9. The semi-circular segments comprising each ring electrode are displaced from the adjacent electrode(s) by 90 degrees. With this arrangement, it is possible to achieve an approximate 90 degree directional resolution by selecting the desired cathode (the active electrode) and anode in the adjacent ring electrode. For example, selection of electrode 91 as cathode and 92 as anode will cause the electric field to have it centre in the approximate region denoted by the "X" in FIG. 9, whereas recruitment of a second anode 93 will cause the field to spread out along the longitudinal axis of the lead and be centred half-way along the axis of electrode 91.

The arrangements described in FIGS. 7 and 9 are ideal for the leads that are designed for neuromodulation of the lPAG and/or vlPAG such as contemplated in the first, second and third aspects of the invention described above wherein the distal electrode group is omitted. In this case, only five and eight connections respectively are required to the IPG.

Device and Implantation

A feature of the implantable pulse generator (IPG) contemplated in this invention is that the IPG is generally more compact that conventional devices as it may require only a single electrode lead wire with relatively few contacts. Furthermore, unilateral implantation in the non-dominant hemisphere of the brain as described in various aspects of this invention simplifies the procedure and reduces the possibility of undesirable side effects.

This arrangement is ideal for a skull mounted IPG implanted in a pocket local to the burr-hole through which the electrodes are routed into the brain. In order for this to be feasible, the IPG should be of the order of 7 cc-8 cc or less and 6 mm-7 mm or less in thickness, approximately one third of the volume of a conventional IPG which would be normally implanted in a chest cavity. Implantation can be achieved by means of a single incision encompassing the region surrounding the burr hole and the IPG pocket. Only a short electrode lead wire is required, preferably less than 40 cm and more preferably less than 30 cm or 20 cm. A short lead wire provides the benefit that the system will be less sensitive to induced currents leading to heating of the electrode/tissue interface during magnetic resonance imaging and the standardised procedure means that this heating can be more reliability characterised by testing prior to implantation.

A skull mounted IPG is therefore the preferred type of device contemplated in this invention but conventional devices may also be employed. Skull implantation permits the procedure to be conducted in one step without removing the stereotactic frame used to position the electrode, which would normally be necessary before repositioning the patent to tunnel electrodes to an IPG site in the chest. Elimination of this step reduces surgical time and reduces risk of infection. Elimination of leads in the neck is beneficial as tissue erosion, discomfort and subsequent movement limitations are is not uncommon in this highly mobile region. The implantation procedure can be completed in a single-stage in three hours or less compared with five to six hours with a conventional IPG.

Figure 10:
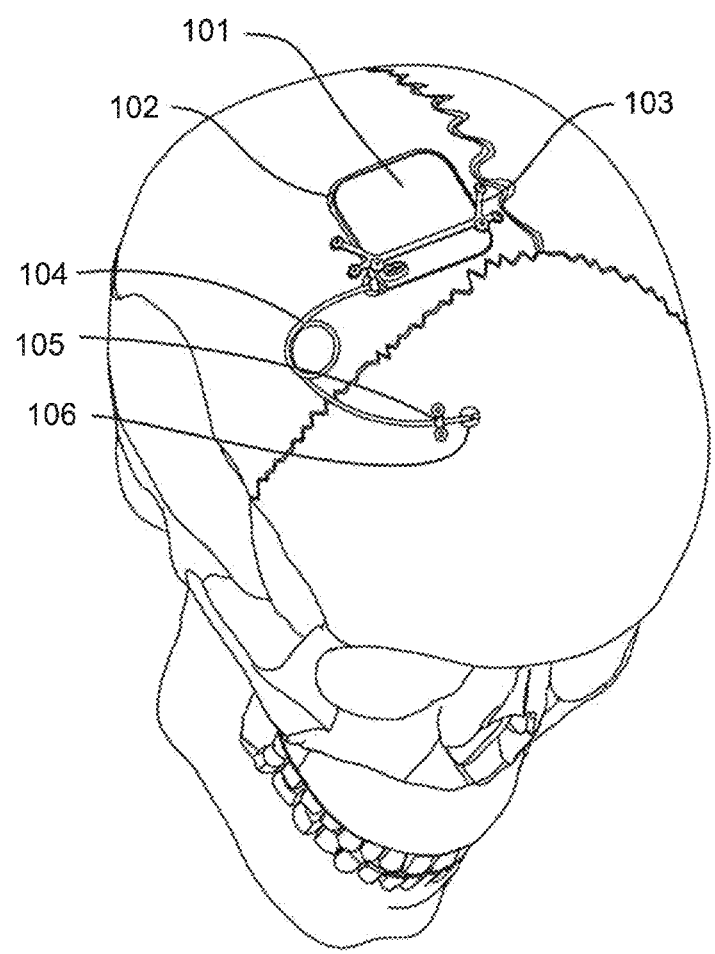
FIG. 10 shows positioning of the implantable pulse generator in a pocket in the frontal-parietal region of the skull and typical unilateral lead placement.

An arrangement for a skull mounted IPG is illustrated in FIG. 10. The IPG, 101, sits in a skull pocket, 102, and is connected to an electrode lead wire, 104, which is routed via a burr hole and optional cap, 106, held securely in place with a lead fixation, 105. The internal placement of the electrodes has been previously discussed as illustrated in FIGS. 4 and 5. In the bilateral case, two lead wires are connected to a single IPG.

Figure 11:
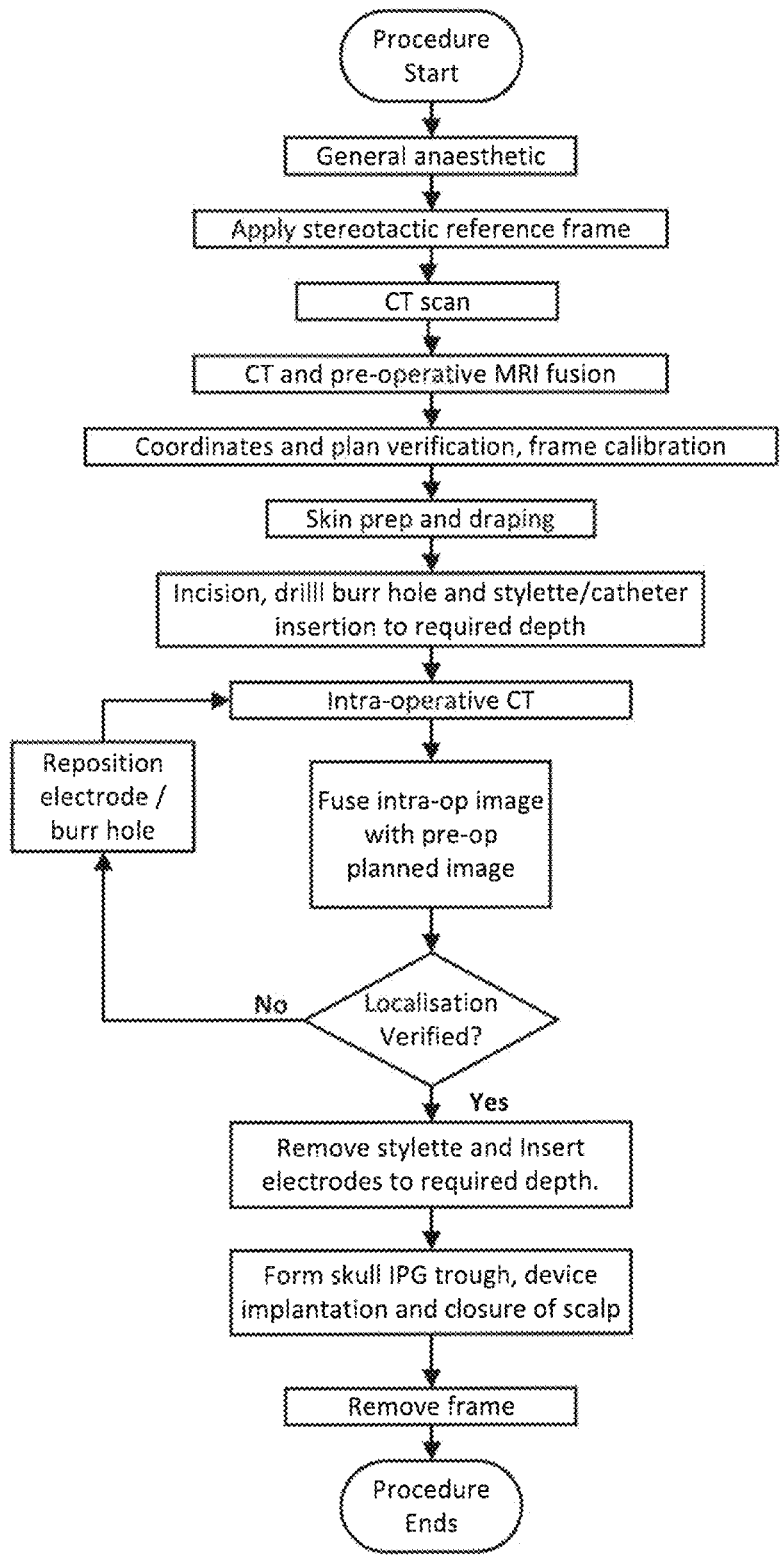
FIG. 11 is a flow-chart illustrating an implantation method employing a skull mounted IPG and implantation of electrode lead-wire(s).

There are many established procedures for implantation of DBS electrodes, the surgical procedure illustrated in FIG. 11 is one such method that employs image guidance and a catheter used as a guide tube to place the electrodes under general anaesthesia.

Prior to or at admission, the patient receives a high resolution MRI scan and post contrast volume scan (highlighting blood vessels) for planning. In advance of the day of surgery, the neurosurgeon plans the entry point and trajectory to span the target sites.

Referring to FIG. 11, on the day of surgical intervention and under general anaesthesia a reference frame is applied and a CT scan is taken with contrast (to identify blood vessels). The high-resolution pre-operative MRI scan and CT scan are fused on planning software, referencing the pre-planned target position relative to the reference frame. 3D co-ordinates are input into the stereotactic frame.

An incision is made on the top of the head encompassing the planned burr hole and IPG pocket site as illustrated in FIG. 10 (or two smaller incisions at the IPG site and burr hole). A burr hole is formed and a guide tube is implanted, and a stylette is introduced down the guide tube to the planned depth, just short of the proximal target. A second burr hole and guide tube may be implanted if desired for bilateral electrodes and the lead tunnelled the short distance under the scalp to the second site.

Sub-millimetre precision at the desired target is necessary to optimise the treatment and avoid side effects. Intra-operative CT enables verification of accurate target localisation. The stylette is withdrawn and the lead inserted down the guide tube to the measured depth encompassing both proximal and distal targets in the case of dual targets. The lead is then secured to the skull with an anchoring device such as a titanium plate (FIG. 10, 105).

A pocket of the IPG dimensions is formed in the frontal-parietal region of the skull. This is machined using a burr and a template to the appropriate depth. The device is secured to the skull with a custom plate, leads are connected and secured and the incision(s) are closed.

This technique typically requires a single pass, is carried out entirely under general anaesthesia and is safer and more accurate than currently established techniques.

A robot may be employed to assist in implantation. In this case the robot may be referenced to fiducials attached to the patient's skull. The robot provides 3D positional guidance for the surgeon when drilling the burr hole and introducing the electrode in the desired trajectory. In a more sophisticated application, the robot may drill the burr hole, introduce the catheter to the planned depth and machine the pocket for the skull mounted IPG.

For treating disease such as post-haemorrhagic vasopasm, where the duration of the condition is short-lived and whilst the patient group is being treated on the intensive care unit, it would be feasible to have the lead externalised and connected to an external pulse generator; or the lead connected to a RF-receiver is implanted into the skull.

REFERENCES

[1] Schenberg, L. C., C. A. Brandao, and E. C. Vasquez, Role of periaqueductal gray matter in hypertension in spontaneously hypertensive rats. Hypertension, 1995. 26(6 Pt 2): p. 1125-8.

[2] Hart, E. C., et al., Translational examination of changes in baroreflex function after renal denervation in hypertensive rats and humans. Hypertension, 2013. 62(3): p. 533-41.

[3] Green, A. L., et al., Deep brain stimulation can regulate arterial blood pressure in awake humans. Neuroreport, 2005. 16(16): p. 1741-5.

[4] Patel, N. K., et al., Deep brain stimulation relieves refractory hypertension. Neurology, 2011. 76(4): p. 405-7.

[5] Pereira, E.A., Lu G, et al., Ventral periaqueductal grey stimulation alters heart rate variability in humans with chronic pain. Exp Neurol, 2010. 223(2): p. 574-81.

[6] Sverrisdottir, Y. B., et al., Differentiated Baroreflex Modulation of Sympathetic Nerve Activity During Deep Brain Stimulation in Humans. Hypertension, 2014.

[7] Patel, N. K., P. Plaha, and S. S. Gill, Magnetic resonance imaging-directed method for functional neurosurgery using implantable guide tubes. Neurosurgery, 2007. 61(5 Suppl 2): p. 358-65; discussion 365-6.

[8] Lyketsos, C G et al. Deep Brain Stimulation: A Novel Strategy for Treating Alzheimer's Disease. Innov Clin Neurosci. 2012; 9(11-12):10-17.

[9] Hamani C, McAndrews M P, Cohn M, Oh M, Zumsteg D, Shapiro C M, et al. Memory enhancement induced by hypothalamic/fornix deep brain stimulation. Ann Neurol. 2008; 63:119-23.

[10] Fontaine D, Deudon A, Lemaire J J, Razzouk M, Viau P, Darcourt J, et al. Symptomatic treatment of memory decline in Alzheimer's disease by deep brain stimulation: a feasibility study. J Alzheimers Dis, 2013; 34:315-23.

[11] Smith G S, Laxton A W, Tang-Wai D F, McAndrews M P, Diaconescu A O, Workman C I, et al. Increased cerebral metabolism after 1 year of deep brain stimulation in Alzheimer Disease. Arch Neurol. 2012; 69:1141-8.

[12] Hardenacke K, Shubina E, Bührle C P, Zapf A, Lenartz D, Klosterkötter J, et al. Deep brain stimulation as a tool for improving cognitive functioning in Alzheimer's dementia: a systematic review. Front Psychiatry, 2013; 4:159

[13] DeD la Torre J C. Alzheimer disease as a vascular disorder: nosological evidence. Stroke. 2002; 33: 1152-1162.

[14] Roher A E et al. Cerebral blood flow in Alzheimer's disease. Vasc Health Risk Manag. 2012; 8: 599-611.

[15] Parvizi J, Van Hoesen GW, Damasio A (2000) Selective pathological changes of the periaqueductal gray matter in Alzheimer's disease. Ann Neurol, 2000; 48:344-353.

[16] Debernard L1, Melzer T R, Van Stockum S, Graham C, Wheeler-Kingshott C A, Dalrymple-Alford J C, Miller D H, Mason D F. Reduced grey matter perfusion without volume loss in early relapsing-remitting multiple sclerosis. JNNP, 2014; 85(5): 544-51

[17] Marshall O, Lu H, Brisset J C, Xu F, Liu P et al. Impaired cerebrovascular reactivity in multiple sclerosis. JAMA Neurol, 2014; 71(10):1275-81

[18] Peruzzo D, Castellaro M, Calabrese M et al. Heterogeneity of cortical lesions in multiple sclerosis: an MRI perfusion study. J Cereb Blood Flow Metab, 2013; 33930: 457-63.

[19] Liu A A, Voss H U, Dyke J P, Heier L A, Schiff N D. Arterial spin labeling and altered cerebral blood flow patterns in the minimally conscious state. Neurology, 2011; 77(16):1518-23

[20] Yamamoto T, Katayama Y, Obuchi T, et al. Deep brain stimulation and spinal cord stimulation for vegetative state and minimally conscious state. World Neurosurg. 2013; 80:3-4

[21] Levy R M, Lamb S, Adams J E. Treatment of chronic pain by deep brain stimulation: long term follow up and review of the literature. Neurosurgery, 1987; 21:885-893.

[22] Shi T et al. L-364,718 Potentiates Electroacupuncture Analgesia Through Cck-A Receptor of Pain-Related Neurons in the Nucleus Parafascicularis. Neurochemical Research. 2011; 36(1):129-38.

The invention claimed is:

1. A method of treating Alzheimer's Disease and/or Multiple Sclerosis and/or Minimally Conscious State and/or Mood Disorders and/or vascular brain disorders where there is small vessel compromise in a subject in need thereof, said subject having previously been diagnosed as suffering from Alzheimer's Disease and/or Multiple Sclerosis and/or Minimally Conscious State and/or Mood Disorders and/or vascular brain disorders where there is small vessel compromise, the method comprising applying a neuromodulation signal to the lPAG or vlPAG of the subject having Alzheimer's Disease and/or Multiple Sclerosis and/or Minimally Conscious State and/or Mood Disorders and/or vascular brain disorders where there is small vessel compromise, wherein the neuromodulation signal has a frequency within the range of 5 to 50 Hz, a stimulus pulse duration within the range of 50 to 450 microseconds, a balanced biphasic waveform with zero net charge flow, and at least one of a stimulus pulse voltage within the range of 1 to 5 volts or a stimulus pulse current within the range of 1 to 5 mA sufficient to stimulate the lPAG or vlPAG.

2. The method according to claim 1, wherein the method is a method of treating vascular brain disorders where there is small vessel compromise in a subject in need thereof, and wherein the vascular brain disorders comprise vascular dementia and/or small vessel disease and/or multiple stroke disease and/or post-haemorrhagic vasospastic disease and/or moyamoya disease.

3. The method according to claim 1, wherein the method includes implanting an electrode lead wire unilaterally into one hemisphere of the brain of the subject to a depth level with the superior colliculus of the subject, the applying of the electrical pulsed signal to the lPAG or vlPAG of the subject being via said electrode lead wire.

4. The method according to claim 3, wherein the method includes externalising the electrode lead wire for a transient period of stimulation and/or connecting the electrode lead wire to a RF-receiver buried in the skull and/or connecting the electrode lead wire to a pulse-generator implanted in the skull.

5. The method according to claim 3, further including applying a further neuromodulation signal to the medial thalamus and/or fornix and/or anterior nucleus and/or the centromedian parafascicular nuclei of the brain of the subject, said further neuromodulation signal being a high frequency signal, and wherein said electrode lead wire is inserted so as to traverse the medial thalamus and/or fornix and/or anterior nucleus of the brain of the subject, and said further neuromodulation signal is applied to said medial thalamus and/or fornix and/or anterior nucleus and/or the centromedian parafascicular nuclei.

6. The method according to claim 3, further including implanting a further electrode lead wire into said one hemisphere, and applying another electrical signal to said further electrode lead wire.

7. The method according to claim 6, wherein the another electrical signal is applied to the medial thalamus and/or fornix and/or anterior nucleus and/or the centromedian parafascicular nuclei of the brain of the subject.

8. The method according to claim 3, further including implanting a further electrode lead wire into the other hemisphere of the brain of said subject to a depth level with the superior colliculus thereof, and applying another electrical pulsed signal to said further electrode lead wire.

9. The method according to claim 1, further including applying a further neuromodulation signal to the medial thalamus and/or fornix and/or anterior nucleus and/or the centromedian parafascicular nuclei of the brain of the subject, said further neuromodulation signal being a high frequency signal.

10. The method according to claim 9, wherein said further neuromodulation signal is a further electrical pulsed signal.

11. The method according to claim 1, further comprising the step of selecting the subject for treatment based on the subject having a diagnosis of Alzheimer's Disease and/or Multiple Sclerosis and/or Minimally Conscious State and/or Mood Disorders and/or vascular brain disorders where there is small vessel compromise in said subject.

12. A method of treating Alzheimer's Disease and/or Multiple Sclerosis and/or Minimally Conscious State and/or Mood Disorders and/or vascular brain disorders where there is small vessel compromise in a subject in need thereof, said subject having previously been diagnosed as suffering from Alzheimer's Disease and/or Multiple Sclerosis and/or Minimally Conscious State and/or Mood Disorders and/or vascular brain disorders where there is small vessel compromise, the method comprising:

applying a neuromodulation signal to the lPAG or vlPAG of the subject having Alzheimer's Disease and/or Multiple Sclerosis and/or Minimally Conscious State and/or Mood Disorders and/or vascular brain disorders where there is small vessel compromise, wherein the neuromodulation signal has a frequency within the range of 5 to 50 Hz, a stimulus pulse duration within the range of 50 to 450 microseconds, a balanced biphasic waveform with zero net charge flow, and at least one of a stimulus pulse voltage within the range of 1 to 5 volts or a stimulus pulse current within the range of 1 to 5 mA sufficient to stimulate the lPAG or vlPAG;

applying a further neuromodulation signal to the medial thalamus and/or fornix and/or anterior nucleus and/or the centromedian parafascicular nuclei of the brain of the subject, wherein said further neuromodulation signal has a frequency greater than 70 Hz, a stimulus pulse duration within the range of 25 to 350 microseconds, a balanced biphasic waveform with zero net charge flow, and at least one of a stimulus pulse voltage within the range of 1 to 3 volts or a stimulus pulse current within the range of 1 to 5 mA sufficient to stimulate at least one of the [lPAG or vlPAG] medial thalamus, fornix, anterior nucleus, or the centromedian parafascicular nuclei.

* * * * *